United States Patent [19]

Wolvek et al.

[11] Patent Number: 4,631,059
[45] Date of Patent: Dec. 23, 1986

[54] SHEATH REMOVER

[75] Inventors: Sidney Wolvek, Brooklyn, N.Y.; Walter Kaiser, Ramsey; Kenneth Kaltenbach, Leonia, both of N.J.

[73] Assignee: Datascope Corp., Oakland, N.J.

[21] Appl. No.: 716,259

[22] Filed: Mar. 26, 1985

[51] Int. Cl.⁴ ............................................. A61M 25/00
[52] U.S. Cl. ................................. 604/280; 604/161; 604/164; 128/348.1; 30/90.4; 30/90.8
[58] Field of Search ...................... 30/90.1, 90.4, 90.7, 30/90.8, 280; 128/1 D, 348.1, 344; 604/280–284, 158–170

[56] References Cited

U.S. PATENT DOCUMENTS

| | | | |
|---|---|---|---|
| 2,141,002 | 12/1938 | Huff | 30/90.7 |
| 3,902,501 | 9/1975 | Citron et al. | 128/419 P X |
| 4,394,828 | 7/1983 | Garbis et al. | 30/90.8 |
| 4,434,554 | 3/1984 | Korbelak | 30/40.8 |
| 4,451,256 | 5/1984 | Weikl et al. | 604/164 |
| 4,473,067 | 9/1984 | Schiff | 128/1 D |

FOREIGN PATENT DOCUMENTS

WO82/03558  10/1982  PCT Int'l Appl. .................. 604/53

Primary Examiner—Dalton L. Truluck
Attorney, Agent, or Firm—Darby & Darby

[57] ABSTRACT

A hollow, open-ended sheath is removed from a position enclosing a catheter which has been inserted through the sheath with a close tolerance and introduced into a human body thereby. A cutting blade is mounted in a deforming and guiding mechanism connected to the blade and engageable with the sheath for exerting pressure on the sheath in such a manner as to deform the sheath away from the catheter at a point immediately adjacent to the cutting blade and into contact with the cutting blade while maintaining the catheter beyond the reach of the blade. The device guides the blade for lengthwise movement relative to the sheath. The blade cuts the sheath in a lengthwise direction for removal from the catheter while the catheter remains in place.

34 Claims, 11 Drawing Figures

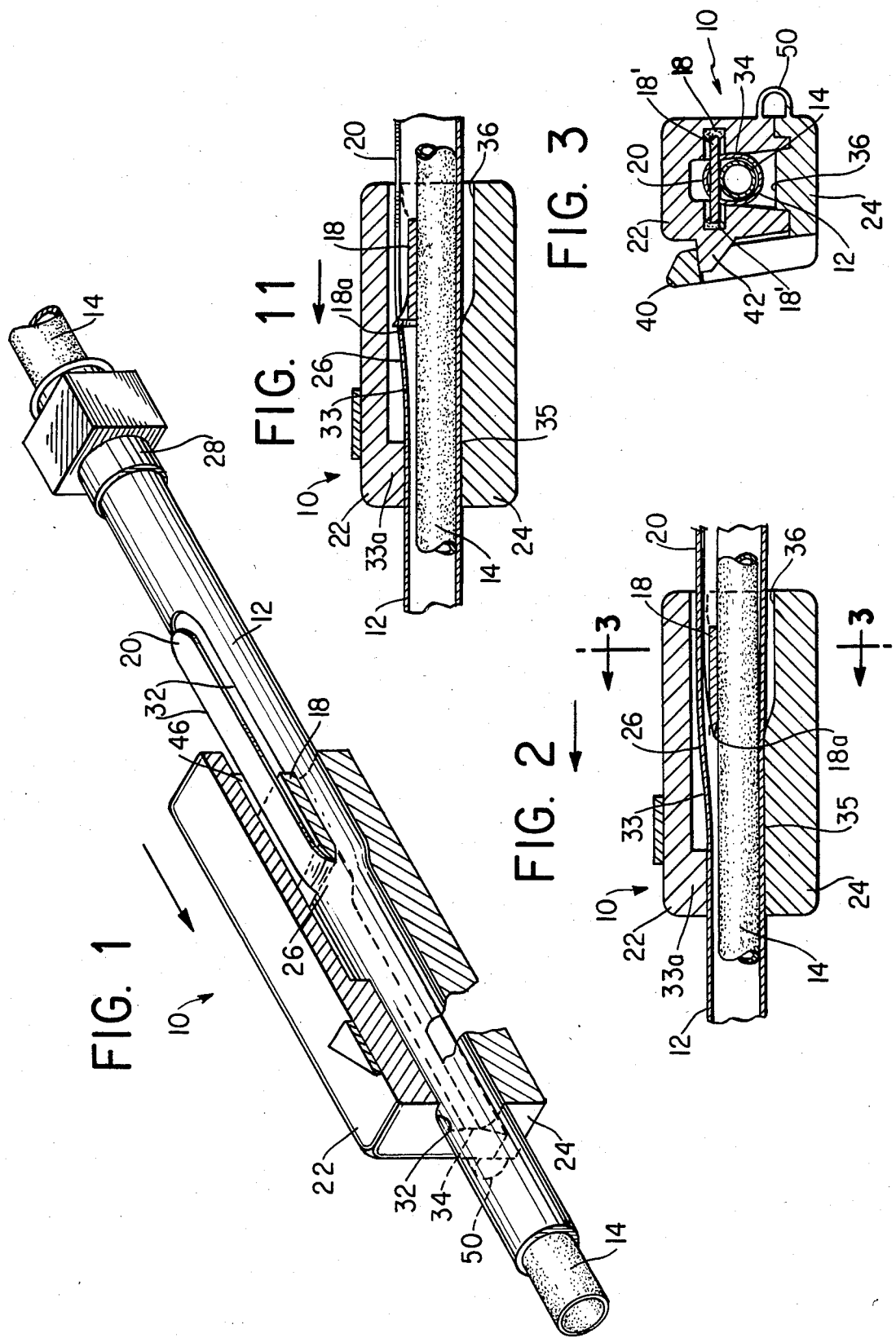

SHEATH REMOVER

BACKGROUND OF THE INVENTION

This invention relates to the removal of sheaths from catheters and, more particularly, to a novel and highly-effective method and apparatus for removing a hollow, open-ended sheath from a position enclosing at least a portion of a catheter which has been inserted through the sheath with a close tolerance and introduced into a human body thereby.

The technique of percutaneously entering the human vascular system with a thin walled flexible sheath was first described by Desilets and Hoffman in 1965. The sheath is hollow and open at both ends and placed into the blood vessel with the aid of a relatively stiff introducer which is initially housed within the sheath and which is removed after the sheath has been inserted. The sheath then acts as a passageway for the insertion of many types of catheters into the vascular system. This includes the placement of intra-aortic balloons, for example, of the types as described in U.S. patent to Hanson and Wolvek U.S. Pat. No. 4,327,709.

The percutaneous introduction of catheters via introducer sheaths has become an established practice in angiography. Angiography catheters in the neighborhood of 4 to 7 French (0.053"–0.092" in diameter) are routinely introduced through introducer sheaths. The advent of the percutaneous intra-aortic balloon has increased dramatically the use of introducer sheaths, as well as their size. These sheaths now accommodate balloon catheters ranging from 8.5 French to 12.5 French (0.112"–0.164" in diameter).

When the introducer sheath is permitted to remain within the artery, surrounding the treatment catheter, the total diameter of the device within the blood vessel is increased by twice the wall thickness of the sheath plus twice the required catheter clearance. In practice, the presence of the introducer sheath may add up to 0.050" to the diameter of the catheter.

Since many treatment catheters such as intra-aortic balloon catheters or ECG pacing lead catheters have enlarged hubs or electronic connections at their proximal ends, the sheath cannot be removed simply by pulling it back along and beyond the catheter and discarding it. In these cases the sheath must actually be cut away or split away from the enclosed catheter. This is generally done by using a scalpel or scissors to cut the sheath away from the catheter. However, the risk of damaging the catheter is always present in such a procedure. The problem being recognized, several attempts have been made to develop a sheath that can be peeled away from the catheter.

The Desilets-Hoffman "Peel Away" introducer sheath has a split proximal end which terminates in two soft flexible "handles." The length of the sheath is scored to encourage splitting away of the sheath simply by pulling the two handles in opposite directions. Another split sheath is the Littleford/Spector introducer (U.S. Pat. No. 4,166,469). This introducer sheath has a T-shaped handle which is reduced in thickness at its centerline, thereby allowing the T-shape to be split by manual pressure. A small punched hole in the sheath material immediately below the splittable portion of the "T" handle, shallow longitudinal groove in the sheath material, perforations, holes, through cuts and reduced wall thicknesses have been described to encourage the longitudinal tearing of the sheath.

Other peelable catheter introducer sheaths have been disclosed which are scored so as to be splittable and which comprise a slidable sleeve to prevent the splitting until the sleeve is slid down the catheter by the physician. These are described by King et al in U.S. Pat. No. 4,412,832 and Boarini et al in U.S. Pat. No. 4,411,654. In both patents no hub assembly is present to form a portion of the introducer sheath.

All of these attempts to solve the problem deny the physician the use of a conventional introducer sheath having a hub containing a female luer at its proximal end. The female luer is present in all non-splittable, conventional introducers and serves multiple important functions. Among these functions is the ability to lock the introducer dilator within the introducer sheath during the actual insertion, by means of their respective luer tapers. After removal of the introducer dilator, the female luer of the introducer sheath can be used for the attachment of a three-way stopcock and syringe for such purposes as blood sampling, the injection of radiographic contrast material, or merely to close the introducer off from the atmosphere. The female luer hub also serves as a "handle" to support the introducer sheath while inserting the catheter within it and helps to control bleeding during the insertion of the catheter.

In addition, the splittable sheaths described above have the potential of splitting accidentally, either because of the internal pressure generated by the passage of a tightly fitting catheter or because of the accidental separation of the splittable handles by the physician. Accidental premature splitting of the sheath while in an artery could result in loss of blood because of the high blood pressures and flows in the arterial system.

SUMMARY OF THE INVENTION

An object of the present invention is to remedy the problems outlined above and, in particular, to permit the physician to use a conventional introducer sheath which may be inserted and used in a conventional manner with no danger of accidental splitting, while reserving to the physician the option to split the sheath for removal from the catheter, should he desire to do so, with no danger of puncturing or otherwise damaging the contained catheter.

The foregoing and other objects are attained in accordance with the invention by providing an attachable and detachable apparatus which can be used when desired for removing a hollow, open-ended sheath from a position enclosing at least a portion of a catheter which has been inserted through the sheath with a close tolerance and introduced into a human body thereby. The apparatus comprises a cutting device and a deforming and guiding device, to which the cutting device is connected, and engageable with the sheath for exerting pressure on the sheath in such a manner as to deform the sheath away from the catheter at a point immediately adjacent to the cutting device and into contact with the cutting device while maintaining the catheter beyond the reach of the cutting device and for guiding the cutting device for lengthwise movement relative to the sheath. As the deforming and guiding means are moved lengthwise along the sheath, the cutting device thus cuts the sheath in a lengthwise direction for removal from the catheter while the catheter remains in place.

BRIEF DESCRIPTION OF THE DRAWING

A better understanding of the invention will be gained from the following detailed description of the preferred embodiments thereof, in conjunction with the appended figures of the drawing, wherein:

FIG. 1 is an isometric perspective view, partly broken away, of a preferred embodiment of apparatus constructed in accordance with the invention, showing its application to an introducer sheath enclosing a catheter;

FIG. 2 is a longitudinal sectional view corresponding to a portion of FIG. 1;

FIG. 3 is a cross section taken along the line 3—3 of FIG. 2 and looking in the direction of the arrows;

FIG. 11 shows another embodiment of the invention in which the blade edge extends vertically toward the sheath.

DESCRIPTION OF THE PREFERRED EMBODIMENTS

Figure 4:
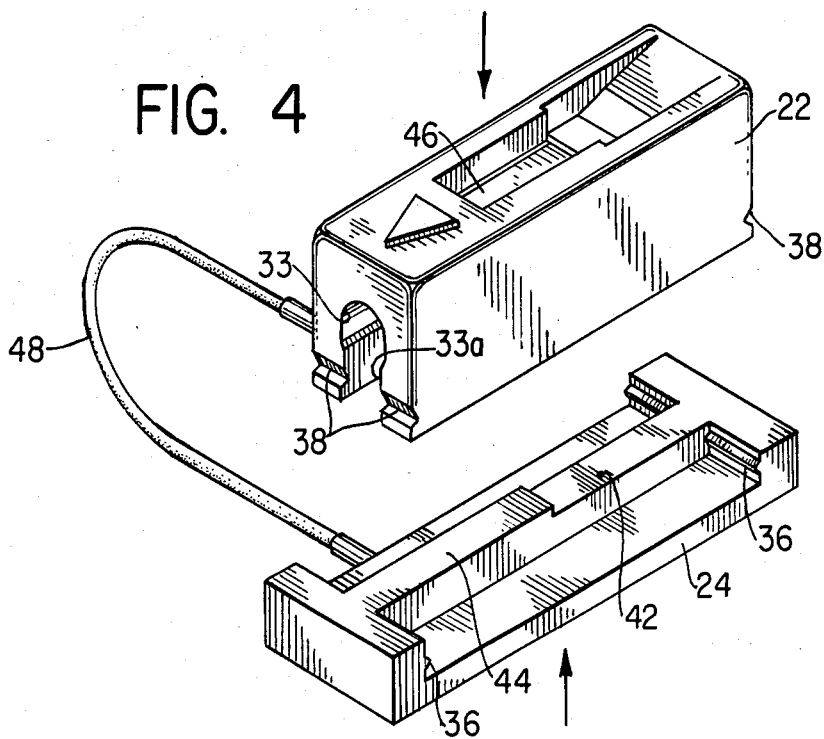
FIG. 4 is an isometric perspective view of another embodiment of apparatus constructed in accordance with the invention, showing two body portions thereof in a disengaged position.

FIGS. 1-3 show a preferred embodiment of the sheath removing apparatus 10 constructed in accordance with the invention. The apparatus 10 is adapted to remove a conventional, hollow, open-ended sheath 12 from a position enclosing at least a portion of a catheter 14 which has been inserted through the sheath 12 with a close tolerance and introduced into a human body 16 thereby (see the diagrammatic illustration in FIGS. 5 and 6). A luer fitting 28 is shown attached to the proximal end of the sheath.

Cutting means such as a blade 18 is mounted in the apparatus 10. The blade 18 is adapted to split the sheath 12, such as by cutting, from a strip 20, in a manner described below, to enable removal of the sheath 12 from the catheter 14 as the apparatus is moved along the length of the sheath in a direction shown by the arrow in FIG. 1.

The apparatus includes deforming and guiding means which in the embodiment of FIGS. 1-3 comprises a first or upper body portion 22 and a second or lower body portion 24 (see FIG. 3) with the blade 18 being mounted in the upper portion 22. The body portion can be of plastic on any other suitable material.

The upper body portion 22 is formed with a groove, or bore 33, with a reduced diameter entrance boss 33a, for receiving the sheath 12 and the catheter 14 it encloses. The first and second body portions 22 and 24 are separable and the sheath is laid in the bore 33 when the two pieces are apart. As shown in FIG. 3, the two body portions are held together by a plastic hinge 50. A latch 40 formed on one, and a mating boss 42 formed on the other, of the body portions 22 and 24 provide a means for securing the two together. The engaged position of the two body pieces is shown in FIGS. 1-3.

The second body portion has an interior wall 35 in the area where the sheath enters the apparatus and a flat 36 stepped below the wall 35, in the area beneath the blade 18. When the second body portion 24 is in engagement with the first body portion 22 and the sheath is laid in the bore 33, the boss 33a of the first portion 22 and the interior wall 35 of the second piece squeeze against and deform the sheath 12 in the area of the flat 36, the portion above the flat where the blade 18 is located being called a cutting zone 26, to separate it from the catheter to provide a free space of the blade to contact the sheath and a disengaged position. Further, as seen in FIG. 3, the interior side walls 31 of the first body portion 22 engage the sheath and squeeze it in a horizontal direction, making it somewhat elliptical in shape. As seen in FIG. 3, a bubble is formed in the sheath below the blade 18 in the cutting zone so that it can cut the sheath without touching the catheter.

The cutting blade 18 is preferably mounted in the first body portion 22 in the area where the sheath is most separated from the catheter. An epoxy cement 18' may be provided for securing the blade 18 therein (FIG. 3). Alternatively, the blade may be secured by heat staking, by potting with an appropriate cement, or by any other suitable means.

The apparatus 10 is separated into its two parts, placed around the sheath 12 adjacent the luer 28 and then the two parts are fastened together. The blade 18 cuts a strip 20 from the sheath 12 as the apparatus 10 is advanced in a distal direction (from the physician towards the patient). The strip 20 is ejected through an exit channel 46 formed in the rear of the first body portion 22. The exit channel 46 discharges the strip 20 in a direction substantially parallel to the lengthwise relative movement of the apparatus 10 with respect to the sheath 12 (FIG. 1).

Figure 5:
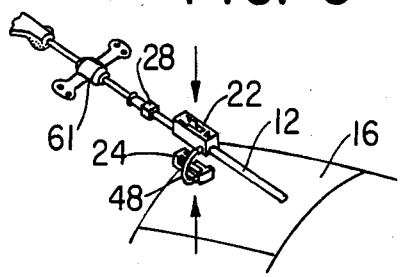
FIG. 5 is a diagrammatic view showing the application of the structure of FIG. 4 to a sheath prior to removal of the sheath.
Figure 6:
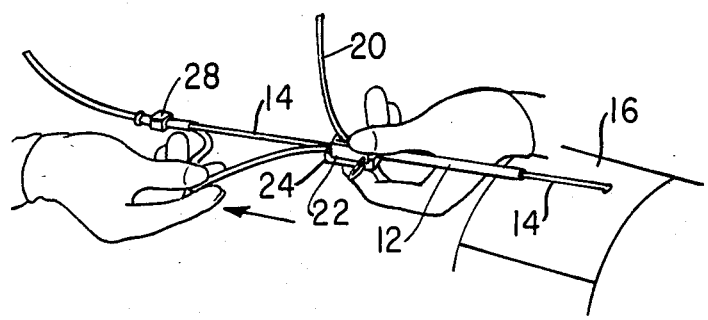
FIG. 6 is a diagrammatic view illustrating removal of the sheath by passing it through the apparatus of the invention with the two body portions thereof in the engaged position.

In practicing the method of the invention, pressure is exerted on the sheath 12 at at least one pressure point in such a manner as to deform the sheath away from the catheter 14 in a given deformation, or cutting, zone such as 26 (FIG. 1 and 2). As seen in FIG. 2, the interior wall portion 34 of the first body portion 22 aids in accomplishing this by squeezing the sheath into a generally elliptical shape after it has been pushed upwardly by the step 30. Relative movement of the apparatus along the sheath 12 continually changes the location of the pressure point, deformation zone and blade 18 in a direction lengthwise of the sheath 12. In this way, the strip 20 is cut from the sheath and the sheath is removable in two separate pieces from the catheter, as shown in FIGS. 5 and 6.

The blade 18 thus cuts the sheath 12 in a lengthwise direction from a proximal location 20' (FIG. 7) to the most distal portion 12' thereof. In this way, the sheath 12 is removed from the catheter 14 while the catheter 14 remains in place (see FIGS. 5 and 6). A knife or scissors may be used to separate the sheath 12 at or near the beginning 20' of the cut which forms the strip 20, thereby leaving the hub 28 residing on the catheter 14.

Figure 7:
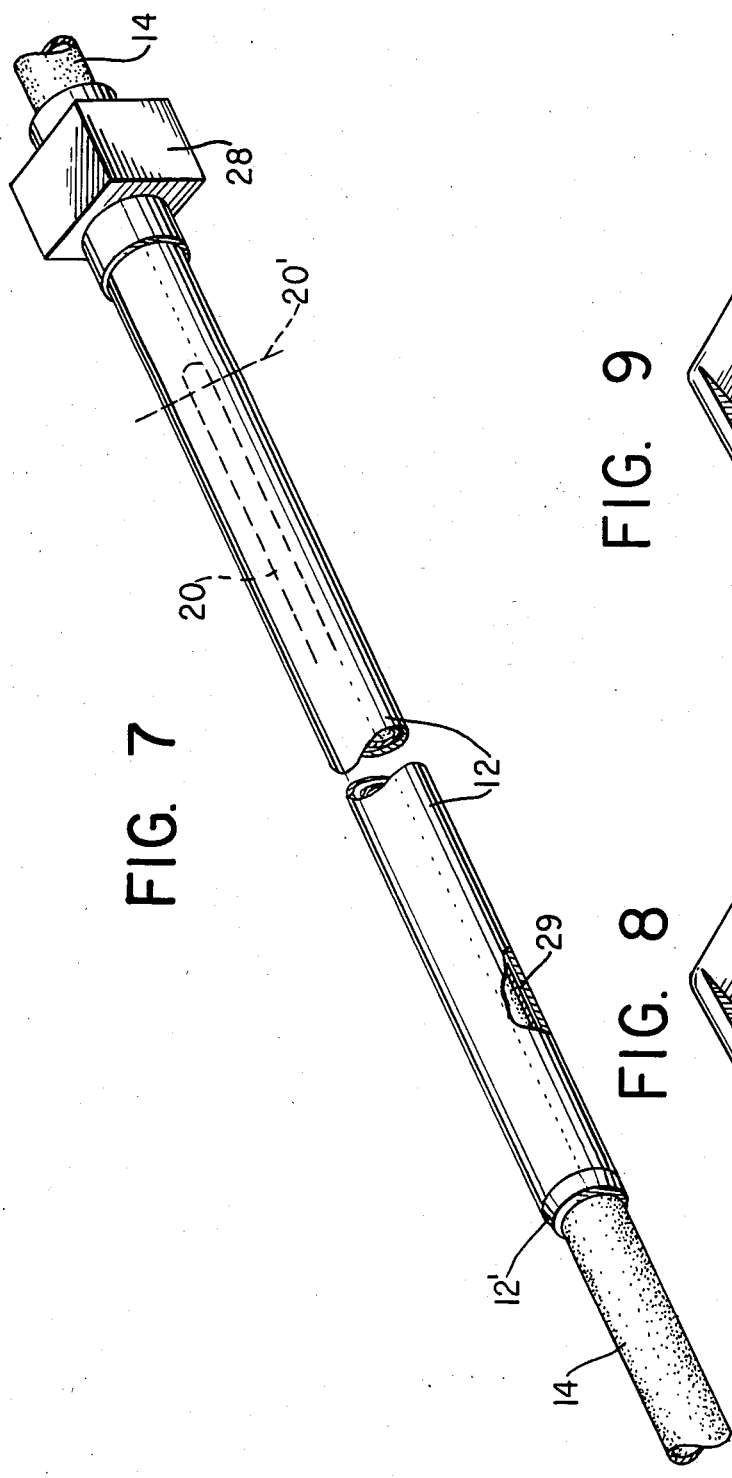
FIG. 7 is an isometric perspective view of a catheter contained within a conventional introducer sheath.

As FIG. 7 shows, there is normally only a very small clearance 29 between the catheter 14 and sheath 12. Typically the clearance may be about 0.01'. By deforming the sheath 12 in accordance with the invention, the normal clearance is increased in the zone 26 so that the blade 18 can cut the sheath 12 with no risk of cutting or otherwise damaging the catheter 14.

As seen from FIGS. 1-3, the upper and lower body portions 22, 24 enclose the blade 18, thereby maintaining the hands of the physician or other operator or user of the apparatus beyond the reach of the blade 18.

The blade 18 has a cutting edge 18a (FIG. 2) which intersects the sheath 12 along two generally parallel lines 32, thereby cutting the sheath into two lengthwise portions, namely the strip 20 and the remainder of the sheath 12 (FIG. 1), which are separately removable from the catheter 14. As described below, other types of cuts can be made.

FIG. 4 shows another embodiment in which the entire groove 33 is formed with a keyway type bore 33 in the upper body portion 22. The sheath and catheter are placed into the apparatus by laying them into the bore 33 and then engaging the two pieces. The bore 33 has a neck 33a for retaining the introducer sheath 12 in the groove 32 when the body portions 22 and 24 are in the disengaged position as shown in FIG. 4. The embodiment of FIG. 4, has snap ribs 36 formed on one, and mating snap grooves 38 formed in the other, of the body portions 22 and 24 to fasten the two pieces together. A length of plastic tubing 48 is connected to each of the two pieces to keep them attached to each other.

The second body portion 24 has a pressure rib 42 (FIG. 4) formed with a pressure plate 44 which bears against and deforms the sheath 12 when the body portions 22 and 24 are in the engaged position. The pressure rib 42 is of reduced height in the cutting zone below the blade 18 to reduce the friction inherent in the lengthwise movement of the device 10 with respect to the sheath 12. If desired, the interior wall of the upper piece also can be formed with the side walls 34 to exert pressure to squeeze the sheath into the elliptical shape.

In the embodiment of FIG. 4, an angled exit channel 46 is formed in the top body portion 22 to discharge the strip 20 in a direction forming an upward angle away from the catheter, but parallel with such lengthwise relative movement.

Figure 8:
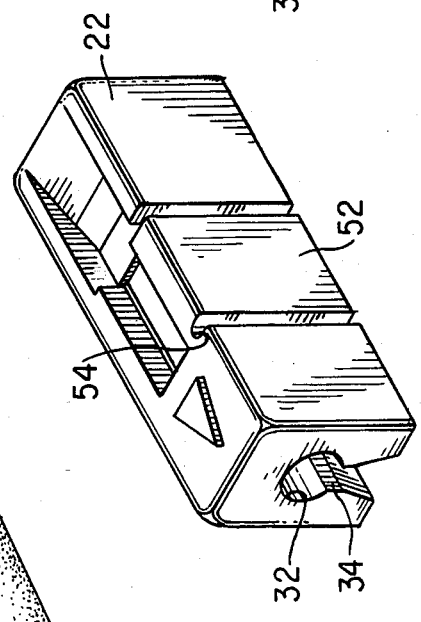
FIG. 8 is an isometric perspective view of another embodiment of the invention.

In the embodiment of FIG. 8, the body portion 22 includes at least one movable portion 52. The movable portion is manually engageable by the user who presses it inwardly to cause it to bear against and deform the sheath 12. A hinge 54 connects the movable portion 52 to the remainder of the body portion 22.

Figure 9:
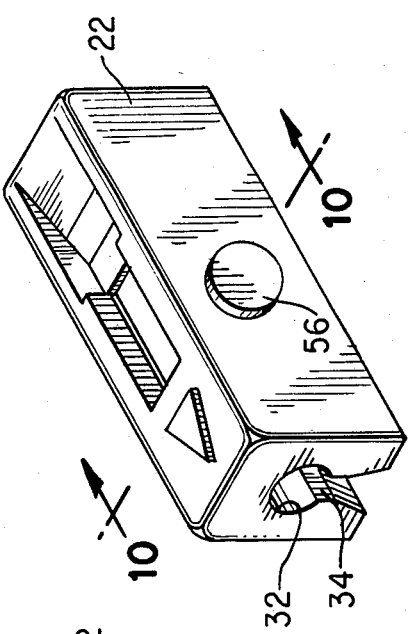
FIG. 9 is an isometric perspective view of still another embodiment of the invention.
Figure 10:
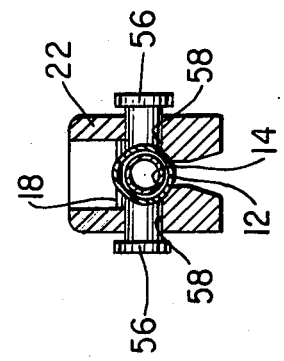
FIG. 10 is a cross section through the line 10—10 of FIG. 9 and looking in the direction of the arrows.

In the embodiment of FIGS. 9 and 10, the body portion 22 comprises a pair of movable portions in the form of buttons 56 slidably arranged in bores 58 respectively on opposite sides of the sheath. Each of the buttons is manually engageable and movable inwardly of the body whereby they are caused to bear against opposite sides of the sheath and deform it upwardly toward the blade 18 to better define the free space between the catheter and the sheath.

Relative movement between the apparatus 10 and the sheath 12 is effected by traction exerted on the sheath or strip 20. The physician exerts such traction by steadying the apparatus 10 with one hand and pulling on the strip 20 or on the other severed portion of the sheath 12, as illustrated in FIG. 6. The sheath 12 is removed without having to pass over enlarged portions of the sheath or catheter which are located proximally with respect to the sheath 12 and which are represented schematically at 28 and 61 in FIG. 5.

FIG. 11 shows another embodiment of the invention. Here, the blade 18a is configured as a V-shaped plow to extend down vertically and forwardly to engage and cut the sheath in the zone 26 where it is deformed away from the catheter. In this embodiment, a single slit is made. A blade arrangement also can be used with two or more vertically downwardly extending blades so that two or more cuts can be made at the same time.

Thus, there is provided in accordance with the invention a novel and highly-effective method and apparatus for removing a sheath from a position enclosing a catheter which has been inserted through the sheath with a close tolerance and introduced into a human body thereby. In accordance with the invention, there is no possibility of accidental cutting of the catheter, since the device in accordance with the invention is constructed so that the catheter remains beyond the reach of the blade. Similarly, since the blade is totally enclosed, the hands of the physician operating the device are also beyond the reach of the blade.

Many modifications of the preferred embodiments of the invention disclosed above will readily occur to those skilled in the art. For example, the materials of which the apparatus 10 is constructed, the orientation of the blade 18 and its spacing from the sheath 12 before the latter is deformed by the apparatus 10, the details of the retaining means for retaining the body portions in the engaged position and of the connecting means for connecting the body portions in the disengaged position can all be varied, as those in the art will readily understand. Accordingly, the invention is to be construed as including all apparatus and methods which fall within the scope of the appended claims.

What is claimed is:

1. Apparatus for removing a hollow, elongated, deformable introducer sheath from a position enclosing at least a portion of a catheter which has been inserted through the sheath with a close tolerance and introduced into a human body thereby, said apparatus comprising cutting means, guiding means carrying said cutting means for moving over said sheath along a selected portion of the length thereof, deforming means on said guiding means engaging the outside of said sheath for exerting pressure thereon in such a manner as to deform a part thereof away from said catheter at a point immediately adjacent to said cutting means and into contact with said cutting means to permit said cutting means to cut through said deformed part of said sheath while maintaining said catheter beyond the reach of said cutting means, whereby said cutting means cuts said sheath in a lengthwise direction as the guiding means moves therealong for removal from said catheter while said catheter remains in place.

2. Apparatus according to claim 1 in combination with an introducer sheath.

3. Apparatus according to claim 1 in combination with an introducer sheath and a catheter.

4. Apparatus according to claim 3 wherein said catheter comprises an enlarged portion proximally located with respect to said sheath, whereby said sheath can be removed from said catheter without passing over said enlarged portion.

5. Apparatus according to claim 3 further comprising a hub connected to said sheath, said hub remaining on said catheter after removal of said sheath.

6. Apparatus according to claim 1 wherein said guiding means encloses said cutting means, thereby maintaining the hands of a user of the apparatus beyond the reach of said cutting means.

7. Apparatus as in claim 1 wherein said cutting means extends vertically inwardly from said guiding means to engage said sheath and make at least one cut in the sheath.

8. Apparatus according to claim 1 wherein said cutting means intersects said sheath along two parallel lines, thereby cutting said sheath into at least two lengthwise portions which are separately removable from said catheter.

9. Apparatus as in claim 8, wherein said cutting means extends generally horizontally from said deforming and guiding means to slice said sheath along the two generally parallel lines.

10. Apparatus according to claim 1 wherein said guiding means comprises
a first body portion formed with a groove for receiving therein an introducer sheath enclosing a catheter.

11. Apparatus according to claim 10 further comprising a second body portion, and means for holding said first and second body portions in an engaged position.

12. Apparatus according to claim 11 wherein said deforming means is on said second body portion and comprises a pressure rib formed with a pressure plate which bears against and deforms said sheath when said body portions are in said engaged position.

13. Apparatus according to claim 12 wherein said pressure rib is of reduced height immediately adjacent to said cutting means in order to reduce the friction inferent in said lengthwise movement of said guiding means.

14. Apparatus according to claim 11 further comprising connecting means connecting said body portions when in a disengaged position.

15. Apparatus according to claim 14 wherein said connecting means comprises a length of plastic tubing.

16. Apparatus according to claim 14 wherein said connecting means comprises a plastic hinge.

17. Apparatus according to claim 10 wherein said first body portion adjacent said groove is formed with a neck for retaining said introducer sheath therein and for deforming the sheath away from said catheter for engagement with said cutting means.

18. Apparatus as in claim 10 further comprising:
a second body portion,
said first and second body portions being separable relative to each other between an engaged position, wherein said second body portion engages said first body portion adjacent said groove in such a manner as to bear against and deform said sheath, and a disengaged position.

19. Apparatus according to claim 18 further comprising retaining means for releasably retaining said body portions in said engaged position.

20. Apparatus according to claim 19 wherein said retaining means comprises snap ribs formed on one, and mating snap grooves formed in the other, of said body portions.

21. Apparatus according to claim 19 wherein said retaining means comprises a latch formed on one, and a mating boss formed on the other, of said body portions.

22. Apparatus according to claim 10 wherein said cutting means is mounted in said first body portion.

23. Apparatus according to claim 22 wherein said cutting means is heat staked in said first body portion.

24. Apparatus according to claim 22 wherein said cutting means cuts a strip from said sheath and said first body portion is formed with an exit channel whereby said strip is discharged from said guiding means.

25. Apparatus according to claim 24 wherein said exit channel discharges said strip in a direction substantially parallel to said lengthwise movement of said guiding means.

26. Apparatus according to claim 24 wherein said exit channel discharges said strip in a direction forming an upward angle but remaining parallel to said lengthwise movement of said guiding means.

27. Apparatus according to claim 1 wherein said guiding means comprises
a body portion formed with a groove for receiving therein the introducer sheath enclosing the catheter, said body portion including at least one movable portion comprising said deforming means, said movable portion being manually engagable to bear against the outside of said sheath to deform it away from said catheter.

28. Apparatus according to claim 27 comprising a hinge connecting said movable portion to the remainder of said body portion.

29. Apparatus according to claim 27 wherein said body portion comprises a pair of movable portions in the form of buttons slidably arranged in bores respectively on opposite sides of said sheath, each of said buttons being manually engageable whereby they are caused to bear against opposite sides of said sheath and deform said sheath.

30. A method of removing a hollow, deformable, elongated introducer sheath from a position enclosing at least a portion of a catheter which has been inserted through the sheath with a close tolerance and introduced into a human body thereby, said method comprising the steps of
exerting pressure externally on the outer surface of said sheath at at least one pressure zone in such a manner as to deform said sheath away from said catheter in a given deformation zone,
bring cutting means to bear against said sheath in said deformation zone to cut through said sheath, and
effecting relative movement of said sheath with respect to said pressure and deformation zones and said cutting means in a direction lengthwise of said sheath,
whereby a cut is made in said sheath and said sheath is removable from said catheter.

31. A method according to claim 30 wherein said relative movement is effected by a concurrent movement of said pressure zone and cutting means.

32. A method according to claim 30 wherein said relative movement is effected by traction exerted on said sheath.

33. A method according to claim 30 wherein said relative movement is effected by traction exerted on said strip.

34. A method according to claim 30 wherein the step of bringing said cutting means to bear includes making two parallel cuts whereof said sheath is removable in two separate pieces from said catheter.

* * * * *